United States Patent
Mori et al.

(10) Patent No.: US 7,388,051 B2
(45) Date of Patent: Jun. 17, 2008

(54) PROPYLENE POLYMER COMPOSITION AND USE THEREOF

(75) Inventors: Ryoji Mori, Sodegaura (JP); Takashi Nakagawa, Sodegaura (JP); Mamoru Kagami, Sodegaura (JP); Akira Todo, Minato-ku (JP)

(73) Assignee: Mitsui Chemicals, Inc., Tokyo (JP)

( * ) Notice: Subject to any disclaimer, the term of this patent is extended or adjusted under 35 U.S.C. 154(b) by 142 days.

(21) Appl. No.: 10/543,360

(22) PCT Filed: Jan. 16, 2004

(86) PCT No.: PCT/JP2004/000292

§ 371 (c)(1), (2), (4) Date: Jul. 26, 2005

(87) PCT Pub. No.: WO2004/067627

PCT Pub. Date: Aug. 12, 2004

(65) Prior Publication Data

US 2006/0057321 A1    Mar. 16, 2006

(30) Foreign Application Priority Data

Jan. 27, 2003 (JP) ............... 2003-016819
Jan. 27, 2003 (JP) ............... 2003-016820

(51) Int. Cl.
C08L 23/10 (2006.01)
C08L 23/02 (2006.01)

(52) U.S. Cl. ............... 525/240; 525/191; 526/351

(58) Field of Classification Search ............... 525/240, 525/191; 526/351
See application file for complete search history.

(56) References Cited

U.S. PATENT DOCUMENTS

| | | | |
|---|---|---|---|
| 5,340,917 A | 8/1994 | Eckman et al. | |
| 6,193,699 B1 | 2/2001 | Matsumoto et al. | |
| 6,255,425 B1 | 7/2001 | Asanuma et al. | |
| 6,576,310 B2 | 6/2003 | Shimada | |
| 6,632,885 B2 * | 10/2003 | Morizono et al. | 525/191 |
| 2001/0021430 A1 | 9/2001 | Shimada | |

FOREIGN PATENT DOCUMENTS

| | | |
|---|---|---|
| EP | 0 414 202 A2 | 2/1991 |
| EP | 0 980 892 A1 | 2/2000 |
| EP | 1 149 598 A2 | 10/2001 |
| EP | 1 275 891 A1 | 1/2003 |
| EP | 1 593 708 A1 | 11/2005 |
| JP | 5-84293 | 4/1993 |
| JP | 2000-63577 | 2/2000 |
| JP | 2000-191858 | 7/2000 |
| JP | 2000-204261 | 7/2000 |
| JP | 2000-334038 | 12/2000 |
| JP | 2001-1432 | 1/2001 |
| JP | 2001-104473 | 4/2001 |
| JP | 2001-172448 | 6/2001 |
| JP | 2001-252348 | 9/2001 |
| JP | 2002-097228 | 4/2002 |
| JP | 2002-097323 | 4/2002 |
| JP | 2002-097325 | 4/2002 |
| JP | 2003-000699 | 1/2003 |
| WO | WO 01/94466 A1 | 12/2001 |

OTHER PUBLICATIONS

Ewen, John A., "Syndiospecific Propylene Polymerizations with Group 4 Metallocenes", *Journal of American Chemical Society*, 1988, vol. 110, pp. 6255-6256.

* cited by examiner

*Primary Examiner*—Randy Gulakowski
*Assistant Examiner*—Olga Asinovsky
(74) *Attorney, Agent, or Firm*—Foley & Lardner LLP (57) ABSTRACT

The invention provides a propylene polymer composition well balanced and excellent in transparency, flexibility, heat resistance, scratch resistance and rubber elasticity, and a medical tube made from the propylene polymer composition. The propylene polymer composition satisfies all the following properties (A), (B), (C) and (D): (A) the composition shows a loss tangent (tan δ) peak at a temperature in the range of −20 to 25° C. according to dynamic viscoelasticity measurement (10 rad/s) in a torsion mode, and the peak is 0.5 or above; (B) the storage elastic modulus G' at 20° C. from the dynamic viscoelasticity measurement is in the range of $1.0 \times 10^7$ to $4.9 \times 10^8$ dyn/cm$^2$; (C) the penetration temperature (° C.) determined in accordance with JIS K 7196 is in the range of 60 to 160° C.; and (D) the composition has a permanent set of not more than 30% as determined after the composition fixed between chucks 30 mm apart is 100% strained at a stress rate of 30 mm/min, maintained for 10 minutes and released for 10 minutes. The medical tube is made from the propylene polymer composition.

4 Claims, 1 Drawing Sheet

Fig. 1

PROPYLENE POLYMER COMPOSITION AND USE THEREOF

FIELD OF THE INVENTION

The present invention relates to a propylene polymer composition, and more particularly to a propylene polymer composition having excellent transparency, flexibility, scratch resistance, heat resistance and rubber elasticity. The invention also relates to a flexible medical tube made from the composition that is suitable for transporting medical fluids such as blood and infusion solutions.

BACKGROUND OF THE INVENTION

Polypropylenes include isotactic polypropylenes and syndiotactic polypropylenes. The isotactic polypropylenes give films that are inexpensive and possess high transparency, toughness, humidity resistance and heat resistance. Such films are therefore widely used as packaging materials. Of the isotactic polypropylene films, ethylene/propylene random copolymer films are particularly excellent in transparency but reduce the transparency and flexibility with increasing film thickness. For example, the film thickness is up to about 60 μm in order to obtain sufficient transparency such that the packaging material does not deteriorate the appearance of content. Accordingly, production of thick polypropylene films high in transparency and flexibility has been difficult.

On the other hand, the syndiotactic polypropylenes are known to be obtained by low temperature polymerization in the presence of a catalyst that includes a vanadium compound, an ether and an organoaluminum. The polymers obtained by this method, however, possess low syndiotacticity and cannot exhibit the inherent syndiotactic properties.

In this connection, J. A. Ewen et al. were the first to find that high-tacticity polypropylenes having a syndiotactic pentad ratio of above 0.7 can be obtained by polymerization in the presence of a catalyst containing a transition metal catalyst with asymmetric ligands and an aluminoxane (J. Am. Chem. Soc., 1988, 110, 6255-6256).

The polymers obtained by the method of J. A. Ewen et al. have high syndiotacticity and are more elastic than the isotactic polypropylenes. However, such flexible forming materials cannot satisfy the flexibility, rubber elasticity and mechanical strength as required in the field where soft vinyl chloride and vulcanized rubbers are used.

Attempts have been widely made to improve the polypropylene's flexibility and impact resistance by incorporating an ethylene/propylene copolymer rubber or the like. Articles from the resin compositions obtained by this method show a certain level of flexibility and impact resistance, but the rubber elasticity and mechanical strength thereof are insufficient.

Medical tubes include tubes for introducing or deriving a substance into or from a body, and catheters inserted into the body for test or treatment. Specific examples of the medical tubes include catheters such as urinary catheters, stomach catheters and suction catheters, tubes such as infusion solution tubes, enteral feeding tubes, peritoneal dialysis tubes, blood transfusion tubes and tubes connected to a urinary catheter to guide urine to a urine collection bag, circuit tubes used in blood circuits for hemodialysis, artificial heart lungs and plasmapheresis, and tubes for transporting substances in the medical field. The transporting tubes for medical substances include tubes attached to multiple blood bags and tubes connecting an aspirator and a catheter. Many of the conventional medical tubes are made from polyvinyl chloride that is inexpensive and possesses excellent kink resistance and a certain level of flexibility (pliancy). However, alternative materials have been required out of consideration to the environment and the like.

The alternatives studied so far include styrene elastomer compositions (JP-A-2000-63577, JP-A-2001-252348 and JP-A-2001-1432), thermoplastic polyurethane compositions (JP-A-H05-84293), and syndiotactic 1,2-polybutadiene compositions (JP-A-2000-334038 and JP-A-2001-104473). The fact, however, is that these compositions have low versatility and practical utility due to insufficient flexibility and high costs.

To achieve the versatility and practical utility, studies have been made on copolymers of ethylene and α-olefins of 3 or more carbon atoms, and acid copolymers of ethylene and vinyl acetate. However, none has satisfied performances required such as flexibility, heat resistance and kink resistance.

Of the polypropylenes such as the isotactic polypropylenes and syndiotactic polypropylenes, the isotactic polypropylenes are inexpensive and excellent in transparency and heat resistance, and are therefore widely used in various packaging materials and industrial materials. However, their flexibility is unsatisfactory. To solve this problem, compositions have been studied in which a flexible material such as an ethylenic elastomer is blended with polypropylene. However, none has satisfied performances as required.

DISCLOSURE OF THE INVENTION

The present invention has been made to solve the above problems in the art. It is therefore an object of the invention to provide a propylene polymer composition well balanced and excellent in transparency, flexibility, heat resistance, scratch resistance and rubber elasticity.

Further, the present inventors made intensive studies of medical tubes excellent in heat resistance, flexibility and kink resistance that are capable of solving the problems in the art, and have arrived at a medical tube having well balanced properties that is obtained from a specific propylene polymer composition.

A propylene polymer composition according to the present invention satisfies all the following properties (A), (B), (C) and (D):

(A) the composition shows a loss tangent (tan δ) peak at a temperature in the range of −20 to 25° C. according to dynamic viscoelasticity measurement (10 rad/s) in a torsion mode, and the peak value is 0.5 or above;

(B) the storage elastic modulus G' at 20° C. from the dynamic viscoelasticity measurement is in the range of $1.0 \times 10^7$ to $4.9 \times 10^8$ dyn/cm$^2$;

(C) the penetration temperature (° C.) determined in accordance with JIS K 7196 is in the range of 60 to 160° C.; and (D) the composition has a permanent set of not more than 30% as determined after the composition fixed between chucks 30 mm apart is 100% strained at a stress rate of 30 mm/min, maintained for 10 minutes and released for 10 minutes.

The propylene polymer composition comprises:

(i) 1 to 40 parts by weight of a syndiotactic polypropylene; and (ii) 60 to 99 parts by weight of a syndiotactic propylene/ethylene copolymer that contains 99 to 55 mol % of a syndiotactic propylene component and 1 to 45 mol % of an ethylene component (the total of the syndiotactic polypropylene (i) and the syndiotactic propylene/ethylene copolymer (ii) is 100 parts by weight);

wherein the composition has a Young's modulus (YM) of not more than 100 MPa as determined in accordance with JIS 6301.

A medical tube according to the present invention comprises the above propylene polymer composition.

In a preferred embodiment, the syndiotactic polypropylene (i) has a $^{13}$C-NMR syndiotactic pentad ratio (rrrr) of 0.5 or above, and a melt flow index (MFI) in the range of 0.1 to 50 g/10 min; and the copolymer (ii) has an intrinsic viscosity [η] of 0.01 to 10 dl/g as determined at 135° C. in decalin, a GPC molecular weight distribution of not more than 4, and a glass transition temperature Tg of not more than −10° C.

The propylene polymer composition has well-balanced and excellent transparency, flexibility, heat resistance, scratch resistance and rubber elasticity.

The propylene polymer composition and the medical tube made from the propylene polymer composition are excellent in the balance of transparency, flexibility, heat resistance, scratch resistance and rubber elasticity, and possess superior kink resistance that has been a problem in the art.

BRIEF DESCRIPTION OF THE DRAWING

FIG. 1 shows an evaluation jig used in the present invention. The evaluation jig is a hollow cylinder (1) having a hole 10 mm in diameter and 5 mm in height. A tube (2) having an inner diameter of 2.1 mm and a length of 20 cm is looped by inserting both ends thereof into the jig, and the ends are slowly pulled down until a kink occurs in the loop. The loop length (H) at the occurrence of kink is obtained as indicator of the kink resistance. The shorter the loop length, the higher the kink resistance.

PREFERRED EMBODIMENTS OF THE INVENTION

Hereinbelow, the propylene polymer composition of the invention will be described in detail.

Propylene Polymer Composition

The propylene polymer composition according to the present invention satisfies all the following properties (A), (B), (C) and (D):

(A) the composition shows a loss tangent (tan δ) peak at a temperature in the range of −20 to 25° C. according to dynamic viscoelasticity measurement (10 rad/s) in a torsion mode, and the peak value is 0.5 or above;

(B) the storage elastic modulus G' at 20° C. from the dynamic viscoelasticity measurement is in the range of $1.0 \times 10^7$ to $4.9 \times 10^8$ dyn/cm$^2$;

(C) the penetration temperature (° C.) determined in accordance with JIS K 7196 is in the range of 60 to 160° C.; and (D) the composition has a permanent set of not more than 30% as determined after the composition fixed between chucks 30 mm apart is 100% strained at a stress rate of 30 mm/min, maintained for 10 minutes and released for 10 minutes.

In the property (A), the loss tangent (tan δ) at −20 to 25° C. is 0.5 or above, preferably in the range of 0.5 to 2.5, and more preferably in the range of 0.6 to 2. When the loss tangent (tan δ) at −20 to 25° C. is lower than 0.5, the composition tends to show insufficient flexibility or, even if having flexibility, tends to be poor in scratch resistance.

In the property (B), the storage elastic modulus G' at 20° C. is in the range of $1.0 \times 10^7$ to $4.9 \times 10^8$ dyn/cm$^2$, preferably in the range of $3.0 \times 10^7$ to $4.9 \times 10^8$ dyn/cm$^2$, and more preferably in the range of $5.0 \times 10^7$ to $4.9 \times 10^8$ dyn/cm$^2$.

When the storage elastic modulus G' at 20° C. is less than $1.0 \times 10^7$ the surface stickiness tends to occur to deteriorate handling properties. When the storage elastic modulus G' exceeds $4.9 \times 10^8$, the product having a large thickness tends to show insufficient flexibility and lower strain recovery from a folded state.

In the property (C), the penetration temperature (° C.) determined in accordance with JIS K 7196 is in the range of 60 to 160° C., preferably in the range of 60 to 150° C., and more preferably in the range of 80 to 140° C. When the penetration temperature is below 60° C., the composition cannot be applied to uses requiring heating and sterilization.

In the property (D), the permanent set is not more than 30%, preferably not more than 25%, and still preferably not more than 20% as determined after a dumbbell specimen 50 mm in length, 15 mm in gauge length, 5 mm in width and 1 mmt in thickness that is fixed between chucks 30 mm apart is 100% strained at a stress rate of 30 mm/min, maintained for 10 minutes and released for 10 minutes. When the permanent set exceeds 30%, the rubber elasticity tends to be low, and the composition cannot be applied to uses requiring stretching properties and recovery properties.

The propylene polymer composition of the invention does not contain any of ethylene/α-olefin block copolymers (a) and aromatic hydrocarbon block copolymers (b).

Ethylene/α-olefin Block Copolymers (a)

The ethylene/α-olefin block copolymers (a) that are not contained in the propylene polymer composition are composed of a low crystalline copolymeric segment and an amorphous copolymeric segment wherein the low crystalline copolymeric segment contains a crystalline polyethylene segment that includes 5 to 40 mol % of a structural unit derived from an olefin of 3 to 10 carbon atoms and 60 to 95 mol % of a structural unit derived from ethylene.

The ethylene/α-olefin block copolymers satisfy all the conditions 1 to 3:

1. The melting point (Tm) obtained from a DSC endothermic curve and the ethylene content (C2) determined by common NMR have a relation of: Tm (° C.)>3.9×C2 (mol %)−230.

2. The molecular weight distribution by GPC is in the range of 1 to 1.5.

3. The component soluble in n-decane at room temperature constitutes 0 to 20 wt %.

The content of the 23° C. n-decane soluble component in the ethylene/α-olefin block copolymers is measured as follows. A 1-liter flask equipped with a stirrer is charged with 3 g of a polymer sample, 20 mg of 2,6-di-tert-butyl-4-methylphenol and 500 ml of n-decane, and is heated on a 145° C. oil bath to dissolve the polymer sample. After the polymer sample has been dissolved, the solution is cooled to room temperature over a period of about 8 hours and is held on a 23° C. water bath for 8 hours. The polymer precipitated is filtered out from the n-decane solution containing the dissolved polymer by means of a G-4 (or G-2) glass filter. The solution is then heated at 10 mmHg and 150° C. to perform drying until a fixed amount is reached of the polymer dissolved in the n-decane solution. The weight is obtained as the content of the 23° C. n-decane soluble component. The content of the 23° C. n-decane soluble component in the ethylene/α-olefin block copolymer is expressed in percentage relative to the weight of the polymer sample.

The olefins of 3 to 20 carbon atoms include propylene, 1-butene, 1-pentene, 1-hexene, 4-methyl-1-pentene, 3-methyl-1-pentene, 1-octene, 3-methyl-1-butene, 1-decene, 1-dodecene, 1-tetradodecene, 1-hexadecene, 1-octadecene, 1-eicosene, cyclopentene, cycloheptene, norbornene, 5-ethyl-2-norbornene, tetracyclododecene and 2-ethyl-1,4,5,8-dimethano-1,2,3,4,4a,5,8,8a-octahydronaphthalene.

The copolymers may contain two or more kinds of the structural units derived from the C3-20 olefins or ethylene.

The ethylene/α-olefin block copolymers may contain up to 5 mol % of a structural unit derived from a diene compound of 4 to 20 carbon atoms.

The diene compounds include 1,3-butadiene, 1,3-pentadiene, 1,4-pentadiene, 1,3-hexadiene, 1,4-hexadiene, 1,5-hexadiene, 4-methyl-1,4-hexadiene, 5-methyl-1,4-hexadiene, 6-methyl-1,6-octadiene, 7-methyl-1, 6-octadiene, 6-ethyl-1,6-octadiene, 6-propyl-1,6-octadiene, 6-butyl-1,6-octadiene, 6-methyl-1,6-nonadiene, 7-methyl-1,6-nonadiene, 6-ethyl-1,6-nonadiene, 7-ethyl-1,6-nonadiene, 6-methyl-1,6-decadiene, 7-methyl-1,6-decadiene, 6-methyl-1,6-undecadiene, 1,7-octadiene, 1,9-decadiene, isoprene, butadiene, ethylidenenorbornene, vinylnorbornene and dicyclopentadiene.

Production of the ethylene/α-olefin block copolymers (a) is disclosed in, for example, JP-A-H05-043770.

Aromatic Hydrocarbon Block Copolymers (b)

The aromatic hydrocarbon block copolymers (b) that are not contained in the propylene polymer composition include aromatic vinyl/conjugated diene block copolymers (b1) having a block polymer unit (X) derived from an aromatic vinyl and a block polymer unit (Y) derived from a conjugated diene, and hydrogenated products thereof (b2).

The aromatic vinyl/conjugated diene block copolymers (b1) of the above structure are for example indicated by X(YX)n or (XY)n (where n is an integer of 1 or greater).

In the styrene block copolymers, the aromatic vinyl block polymer units (X), which are hard segments, are present as crosslinking points for the conjugated diene block polymer units (Y) to form a physically crosslinked structure (domain) The conjugated diene block polymer units (Y) present among the aromatic vinyl block polymer units (X) are soft segments and have rubber elasticity.

The aromatic vinyls for the block polymer units (X) include styrene and styrene derivatives such as α-methylstyrene, 3-methylstyrene, p-methylstyrene, 4-propylstyrene, 4-dodecylstyrene, 4-cyclohexylstyrene, 2-ethyl-4-benzylstyrene and 4-(phenylbutyl)styrene. The conjugated dienes for the block polymer units (Y) include butadiene, isoprene, pentadiene, 2,3-dimethylbutadiene and combinations thereof. When the conjugated diene block polymer units (Y) are derived from butadiene and isoprene, the isoprene- and butadiene-derived units are contained in an amount of 40 mol % or more. The conjugated diene block polymer unit (Y) maybe any of a random copolymer unit, a block copolymer unit and a tapered copolymer unit. The content of the aromatic vinyl polymer units may be determined by a common method such as infrared spectroscopy or NMR spectroscopy. The hydrogenated products (b2) of aromatic vinyl/conjugated diene block copolymers may be obtained by hydrogenating the above aromatic vinyl/conjugated diene block copolymers (b1) by a common method. The hydrogenated products (b2) of the aromatic vinyl/conjugated diene block copolymers generally have a hydrogenation ratio of 90% or above. The hydrogenation ratio is a value relative to the total content (100%) of carbon-carbon double bonds in the conjugated diene block polymer units (Y).

The hydrogenated products (b2) of the aromatic vinyl/conjugated diene block copolymers include hydrogenated styrene/isoprene block copolymer (SEP), hydrogenated styrene/isoprene/styrene block copolymer (SEPS; polystyrene/polyethylene/propylene/polystyrene block copolymer) and hydrogenated styrene/butadiene block copolymer (SEBS; polystyrene/polyethylene/butylene/polystyrene block copolymer). Specific examples include products commercially available under the trade names of HYBRAR (manufactured by KURARAY CO., LTD.), KRATON (manufactured by SHELL CHEMICALS LIMITED), CALIFLEX TR (manufactured by SHELL CHEMICALS LIMITED), SOLPRENE (manufactured by Phillips Petroleum Company), EUROPRENE SOLT (manufactured by ANIC), TUFPRENE (manufactured by Asahi Kasei Chemicals Corporation), SOLPRENE-T (manufactured by JAPAN ELASTOMER CO., LTD.), JSR-TR (manufactured by JSR CORPORATION), DENKA STR (manufactured by DENKI KAGAKU KOGYO KABUSHIKI KAISHA), QUINTAC (manufactured by ZEON CORPORATION), KRATON G (manufactured by SHELL CHEMICALS LIMITED) and TUFTEC (manufactured by Asahi Kasei Chemicals Corporation).

The propylene polymer composition having the aforesaid properties (A) to (D) preferably contains a propylene polymer (i) and a syndiotactic propylene/ethylene copolymer (ii). The propylene polymer (i) is an isotactic polypropylene or a syndiotactic polypropylene, and is preferably a syndiotactic polypropylene. The propylene polymer composition contains the propylene polymer (i) in an amount of 1 to 40 parts by weight, and preferably 5 to 30 parts by weight, and the syndiotactic propylene/ethylene copolymer (ii) in an amount of 60 to 99 parts by weight, and preferably 70 to 95 parts by weight. The syndiotactic propylene/ethylene copolymer (ii) preferably has a propylene content of 99 to 55 mol %, more preferably 95 to 60 mol %, and still preferably 90 to 70 mol %. The stereoregularity of the α-olefin segment may be atactic, isotactic or syndiotactic without limitation, and is preferably syndiotactic. The α-olefin content and stereo regularity can be known by common NMR. In a particularly preferred embodiment, the propylene polymer composition is a syndiotactic propylene polymer composition as described below.

Syndiotactic Propylene Polymer Composition

The propylene polymer composition of the invention preferably comprises:

(i) 1 to 40 parts by weight of a syndiotactic polypropylene; and (ii) 60 to 99 parts by weight of a syndiotactic propylene/ethylene copolymer that contains 99 to 55 mol % of a syndiotactic propylene component and 1 to 45 mol % of an ethylene component (the total of the syndiotactic polypropylene (i) and the syndiotactic propylene/ethylene copolymer (ii) is 100 parts by weight);

wherein the composition has a Young's modulus (YM) of not more than 100 MPa as determined in accordance with JIS 6301.

The propylene polymer composition may further contain a terpene resin or petroleum resin, or a hydrogenated derivative thereof (iii) that has a weight-average molecular weight (Mw) of 500 to 10000. In the above case, the propylene polymer composition contains:

(i) 1 to 40 parts by weight of a syndiotactic polypropylene;

(ii) 59 to 98 parts by weight of a syndiotactic propylene/ethylene copolymer that contains 99 to 55 mol % of a syndiotactic propylene component and 1 to 45 mol % of an ethylene component; and (iii) 1 to 30 parts by weight of a terpene resin or petroleum resin, or a hydrogenated derivative thereof that has a weight-average molecular weight (Mw) of 500 to 10000; and the composition has a Young's modulus (YM) of not more than 100 MPa as determined in accordance with JIS 6301.

The components (i) and (ii) contained in the propylene polymer composition will be discussed below.

(i) Syndiotactic Polypropylene

The syndiotactic polypropylene (i) may contain a small amount of copolymerized units derived from ethylene or an α-olefin of 4 or more carbon atoms, in an amount of not more than 20 wt %, and preferably not more than 15 wt %.

The syndiotactic polypropylene can be prepared by using a catalyst, for example a metallocene catalyst disclosed in JP-A-H02-41303.

The syndiotactic pentad ratio (rrrr, pentad syndiotacticity) is 0.5 or above, preferably 0.6 or above, more preferably 0.7 or above, and particularly preferably 0.80 or above. The syndiotactic polypropylene with a syndiotactic pentad ratio of 0.5 or above is excellent in heat resistance and forming properties, and shows good characteristics as crystalline polypropylene.

The syndiotactic pentad ratio (rrrr) is obtained from the formula (1):

$$rrrr \text{ fraction} = Prrrr/PW \tag{1}$$

wherein Prrrr is an absorption intensity in a $^{13}$C-NMR spectrum assigned to the methyl group of the third unit in five sequential syndiotactic propylene units, and Pw is the total of absorption intensities in a $^{13}$C-NMR spectrum assigned to all the methyl groups of the propylene units.

NMR measurement is carried out as follows: 0.35 g of a sample is dissolved in 2.0 ml of hexachlorobutadiene by heating. The solution is filtered through a glass filter (G2) and 0.5 ml of deuterated benzene is added to the filtrate. The mixture is placed in an NMR tube having an inner diameter of 10 mm, and $^{13}$C-NMR measurement is carried out at 120° C. using NMR apparatus GX-500 manufactured by JEOL. The measurement is performed 10,000 scans or more.

The melt flow index (MFI, 190° C., 2.16 kg load) of the syndiotactic polypropylene is desirably 0.1 to 50 g/10 min, preferably 0.1 to 30 g/10 min, and more preferably 0.1 to 20 g/10 min. When MFI is in the above range, the syndiotactic polypropylene tends to show good flowability and be easily miscible with other components. Further, the composition obtained will give formed products having high mechanical strength.

The density of the syndiotactic polypropylene is desirably 0.86 to 0.91 g/cm$^3$, and preferably 0.865 to 0.90 g/cm$^3$. The syndiotactic polypropylene having this density tends to exhibit good forming properties and give formed products with sufficient flexibility.

(ii) Syndiotactic Propylene/Ethylene Copolymer

The syndiotactic propylene/ethylene copolymer contains a syndiotactic propylene component in an amount of 99 to 55 mol %, preferably 95 to 60 mol %, and particularly preferably 90 to 65 mol %, and an ethylene component in an amount of 1 to 45 mol %, preferably 5 to 40 mol %, and particularly preferably 10 to 35 mol %. Containing the ethylene and propylene components in the above amounts, the syndiotactic propylene/ethylene copolymer (ii) tends to show good compatibility with the syndiotactic polypropylene. Further, the propylene polymer composition obtained will exhibit adequate transparency, flexibility, heat resistance and scratch resistance.

The intrinsic viscosity [η] of the syndiotactic propylene/ethylene copolymer (ii) is desirably in the range of 0.01 to 10 dl/g, and preferably 0.05 to 10 dl/g as determined at 135° C. in decalin. The syndiotactic propylene/ethylene copolymer (ii) having this intrinsic viscosity [η] will show superior characteristics such as weather resistance, ozone resistance, thermal aging resistance, low temperature properties and dynamic fatigue resistance.

The syndiotactic propylene/ethylene copolymer (ii) desirably has a single glass transition temperature, and the glass transition temperature Tg, is desirably −10° C. or less, and preferably −15° C. or less as measured with a differential scanning calorimeter (DSC). The syndiotactic propylene/ethylene copolymer (ii) having the above glass transition temperature Tg has excellent cold resistance and low temperature properties.

The GPC molecular weight distribution (Mw/Mn in terms of polystyrene, Mw: weight-average molecular weight, Mn: number-average molecular weight) is preferably 4.0 or less.

The $^{13}$C-NMR spectrum of the syndiotactic propylene/ethylene copolymer recorded using a 1,2,4-trichlorobenzene solution shows a peak near 20.2 ppm that has a relative intensity ratio of 0.3 or above, preferably 0.5 or above, and particularly preferably 0.6 or above relative to the peak intensities assigned to all the methyl groups of the propylene units. When the ratio is 0.3 or above, excellent transparency, scratch resistance and impact resistance can be achieved.

The syndiotactic structure can be determined as follows: 0.35 g of a sample is dissolved in 2.0 ml of hexachlorobutadiene by heating. The solution is filtered through a glass filter (G2) and 0.5 ml of deuterated benzene is added to the filtrate. The mixture is placed in an NMR tube having an inner diameter of 10 mm, and $^{13}$C-NMR measurement is carried out at 120° C. using NMR apparatus GX-500 manufactured by JEOL. The measurement is performed 10,000 scans or more.

Production of Syndiotactic Propylene/Ethylene Copolymer (ii)

The syndiotactic propylene/ethylene copolymer (ii) can be produced using the same metallocene catalyst as used for preparation of the syndiotactic polypropylene (i) or a catalyst described in Japanese Patent Application No. 2002-332243, although not limited thereto.

Terpene Resin, Petroleum Resin or Hydrogenated Derivative Thereof (iii)

The terpene resin or petroleum resin, or the hydrogenated derivative thereof (iii) desirably has a weight-average molecular weight of 500 to 10000, preferably 500 to 7000, and more preferably 500 to 5000, and a glass transition temperature (Tg) obtained from a DSC endothermic curve in the range of 30 to 100° C., preferably 40 to 100° C., and more preferably 50 to 100° C.

The terpene resin or petroleum resin, or the hydrogenated derivative thereof having the above characteristics shows high resistance to heat and discoloration, and enables the composition to exhibit high transparency, scratch resistance and stress relaxation properties.

A formed product of the propylene polymer composition desirably has a degree of cloudiness (haze) of not more than 25%, and preferably not more than 20% as measured in accordance with ASTM D 1003.

The formed product of the propylene polymer composition desirably has a Young's modulus (YM) of not more than 100 MPa, and preferably not more than 80 MPa as determined in accordance with JIS 6301.

The propylene polymer composition of the invention generally has a melt flow rate (ASTM D 1238, 230° C., 2.16 kg load) of 0.0001 to 1000 g/10 min, preferably 0.0001 to 900 g/10 min, and more preferably 0.0001 to 800 g/10 min, and an intrinsic viscosity [η] of 0.01 to 10 dl/g, preferably 0.05 Lo 10 dl/g, and more preferably 0.1 to 10 dl/g as determined at 135° C. in decahydronaphthalene.

The melt tension (MT) of the propylene polymer composition is generally in the range of 0.5 to 10 g, and preferably 1 to 10 g, leading to excellent forming properties into films and tubes. The melt tension (MT) is a tension applied to a filament (strand) when the filament being extruded at 200° C. and an extrusion speed of 15 mm/min is withdrawn at a constant rate (10 m/min), and is measured with a melt tension tester (manufactured by Toyo Seiki Seisaku-Sho, Ltd.).

Production of Propylene Polymer Composition

To produce the propylene polymer composition, the aforementioned components can be mixed in the specified amounts by a number of known processes, for example by mixing by means of a Henschel mixer, a V-type blender, a ribbon blender or a Tumbler mixer, or by mixing as above and melt-kneading the mixture with a single screw extruder, a twin screw extruder, a kneader or a Banbury mixer, followed by granulating or pulverizing.

The propylene polymer composition may contain additives as required while still achieving the objects of the invention. Examples of the additives include weathering stabilizers, heat stabilizers, antistatic agents, anti-slip agents, anti-blocking agents, anti-fogging agents, lubricants, pigments, dyes, plasticizers, anti-aging agents, hydrochloric acid absorbers and antioxidants. Further, "other copolymers" (elastomers) described hereinbelow may be used without departing from the scope of the invention and while still achieving the objects of the invention.

Other Copolymers

The propylene polymer composition may contain "other polymers" (elastomers or elastomer resins) as required.

Examples of the "other copolymers" include ethylene/α-olefin random copolymers (A), ethylene/diene copolymers (E) and ethylene/triene copolymers (F). These copolymers may be used singly or in combination of two or more kinds.

The "other copolymer" may be used in an amount of 0 to 30 parts by weight per 100 parts by weight of the syndiotactic polypropylene polymer. Addition of the "other copolymer" in the above amount enables the composition to give formed products having an excellent balance in flexibility, transparency and low temperature impact resistance.

Ethylene/α-Olefin Random Copolymers (A)

Preferred ethylene/α-olefin random copolymers (A) for use in the invention are soft ethylene/α-olefin copolymers having a density of 0.860 to less than 0.895 g/cm$^3$, preferably 0.860 to 0.890 g/cm$^3$, and a melt flow rate (MFR; ASTM D 1238, 190° C., 2.16 kg load) of 0.5 to 30 g/10 min, preferably 1 to 20 g/10 min.

The α-olefins to be copolymerized with ethylene include those of 3 to 20 carbon atoms, such as propylene, 1-butene, 1-pentene, 1-hexene, 1-heptene, 1-octene, 1-nonene, 1-decene, 1-undecene, 1-dodecene, 1-hexadodecene, 1-octadecene, 1-nonadecene, 1-eicosene and 4-methyl-1-pentene. Of these, the α-olefins of 3 to 10 carbon atoms are preferred. The α-olefins may be used singly or in combination of two or more kinds.

The ethylene/α-olefin random copolymers (A) desirably contain 60 to 90 mol % of a unit derived from ethylene and 10 to 40 mol % of a unit derived from the C3-20 α-olefin.

The ethylene/α-olefin random copolymers (A) may further contain a unit derived from other polymerizable monomer while still achieving the objects of the invention.

Examples of such polymerizable monomers include vinyl compounds such as styrene, vinylcyclopentene, vinylcyclohexane and vinylnorbornane; vinyl esters such as vinyl acetate; unsaturated organic acids such as maleic anhydride and derivatives of the unsaturated organic acids; conjugated dienes such as butadiene, isoprene, pentadiene and 2,3-dimethylbutadiene; and non-conjugated polyenes such as 1,4-hexadiene, 1,6-octadiene, 2-methyl-1,5-hexadiene, 6-methyl-1,5-heptadiene, 7-methyl-1,6-octadiene, dicyclopentadiene, cyclohexadiene, dicyclooctadiene, methylenenorbornene, 5-vinylnorbornene, 5-ethylidene-2-norbornene, 5-methylene-2-norbornene, 5-isopropylidene-2-norbornene, 6-chloromethyl-5-isopropenyl-2-norbornene, 2,3-diisopropylidene-5-norbornene, 2-ethylidene-3-isopropylidene-5-norbornene and 2-propenyl-2,2-norbornadiene.

The ethylene/α-olefin random copolymers (A) may contain the unit derived from the above polymerizable monomer in an amount of 10 mol % or less, preferably 5 mol % or less, and more preferably 3 mol % or less.

Specific examples of the ethylene/α-olefin random copolymers (A) include ethylene/propylene random copolymer, ethylene/1-butene random copolymer, ethylene/propylene/1-butene random copolymer, ethylene/propylene/ethylidenenorbornene random copolymer, ethylene/1-hexene random copolymer and ethylene/1-octene random copolymer. Of these, the ethylene/propylene random copolymer, ethylene/1-butene random copolymer, ethylene/1-hexene random copolymer and ethylene/1-octene random copolymer are particularly preferable. These copolymers may be used in combination of two or more kinds.

The ethylene/α-olefin random copolymers (A) used in the invention generally have a degree of crystallinity of not more than 40%, preferably in the range of 0 to 39%, and more preferably 0 to 35% according to X ray diffractometry.

The ethylene/α-olefin random copolymers may be produced by known methods using vanadium catalysts, titanium catalysts or metallocene catalysts.

The ethylene/α-olefin random copolymer (A) may be contained in the propylene polymer composition in an amount of 0 to 40 wt %, and preferably 0 to 35 wt %. Containing the ethylene/α-olefin random copolymer (A) in this amount, the composition can give formed products having an excellent balance in toughness, hardness, transparency and impact resistance.

Ethylene/Diene Copolymers (E)

The ethylene/diene copolymers (E) used as elastomers in the invention are random copolymers of ethylene and dienes.

The dienes to be copolymerized with ethylene include non-conjugated dienes such as dicyclopentadiene, 1,4-hexadiene, cyclooctadiene, methylenenorbornene and ethylidenenorbornene; and conjugated dienes such as butadiene and isoprene. Of these, butadiene and isoprene are preferred. These dienes may be used singly or in combination of two or more kinds.

The ethylene/diene copolymers (E) desirably contain a diene-derived structural unit in an amount of 0.1 to 30 mol %, preferably 0.1 to 20 mol %, and more preferably 0.5 to 15 mol %. The iodine value thereof is desirably in the range of 1 to 150, preferably 1 to 100, and more preferably 1 to 50. The ethylene/diene copolymers (E) desirably have an intrinsic viscosity [$\eta$] of 0.01 to 10 dl/g, preferably 0.05 to 10 dl/g, and more preferably 0.1 to 10 dl/g as determined at 135° C. in decahydronaphthalene. The ethylene/diene copolymers (E) can be produced by known methods.

The ethylene/diene copolymer (E) may be contained in the propylene polymer composition in an amount of 0 to 40 wt %, and preferably 0 to 35 wt %. Containing the ethylene/diene copolymer (E) in this amount, the composition can give formed products having an excellent balance in toughness, hardness, transparency and impact resistance.

Ethylene/Triene Copolymers (F)

The ethylene/triene copolymers (F) used as elastomers in the invention are random copolymers of ethylene and trienes.

The trienes to be copolymerized with ethylene include non-conjugated trienes such as 6,10-dimethyl-1,5,9-undecatriene, 4,8-dimethyl-1,4,8-decatriene, 5,9-dimethyl-1,4,8-decatriene, 6,9-dimethyl-1,5,8-decatriene, 6,8,9-trimethyl-1,5,8-decatriene, 6-ethyl-10-methyl-1,5,9-undecatriene, 4-ethylidene-1,6-octadiene, 7-methyl-4-ethylidene-1,6-octadiene, 4-ethylidene-8-methyl-1,7-nonadiene (EMND), 7-methyl-4-ethylidene-1,6-nonadiene, 7-ethyl-4-ethylidene-1,6-nonadiene, 6,7-dimethyl-4-ethylidene-1,6-octadiene, 6,7-dimethyl-4-ethylidene-1,6-nonadiene, 4-ethylidene-1,6-decadiene, 7-methyl-4-ethylidene-1,6-decadiene, 7-methyl-6-propyl-4-ethylidene-1,6-octadiene, 4-ethylidene-1,7-nonadiene, 8-methyl-4-ethylidene-1,7-nonadiene and 4-ethylidene-1,7-undecadiene; and conjugated trienes such as 1,3,5-hexatriene. These trienes may be used singly or in combination of two or more kinds.

The trienes may be produced by known methods as disclosed in EP 0691354 A1 and WO 96/20150.

The ethylene/triene copolymers (F) desirably contain a triene-derived structural unit in an amount of 0.1 to 30 mol %, preferably 0.1 to 20 mol %, and more preferably 0.5 to 15 mol %. The iodine value thereof is desirably in the range of 1 to 200, preferably 1 to 100, and more preferably 1 to 50.

The ethylene/triene copolymers (F) desirably have an intrinsic viscosity [$\eta$] of 0.01 to 10 dl/g, preferably 0.05 to 10 dl/g, and more preferably 0.1 to 10 dl/g as determined at 135° C. in decahydronaphthalene.

The ethylene/triene copolymers (F) can be produced by known methods. The ethylene/triene copolymer (F) may be contained in the propylene polymer composition in an amount of 0 to 40 wt %, and preferably 0 to 35 wt %. Containing the ethylene/triene copolymer (F) in this amount, the composition can give formed products having an excellent balance in toughness, hardness, transparency and impact resistance.

Formed Products

The propylene polymer composition of the present invention can be used widely in conventional applications of polyolefins. In particular, the polyolefin composition can be formed into products of various shapes such as sheets, unoriented or oriented films and filaments.

Examples of the formed products include those manufactured by known thermoforming processes such as extrusion, injection molding, blown-film extrusion, blow molding, extrusion blow molding, injection blow molding, press molding, vacuum forming, calendering and foam molding. Several examples will be presented below to describe the formed products.

Extruded products according to the present invention are not particularly limited in shape and product variety, and examples thereof include sheets, (unoriented) films, pipes, hoses, wire coatings and tubes, with sheets (skin materials), films and tubes being preferred.

Extrusion of the propylene polymer composition can employ a common extruder and extrusion conditions. For example, the propylene polymer composition can be molten in a single screw extruder, a kneading extruder, a ram extruder or a gear extruder and be extruded through a predetermined die into a desired shape.

Injection molded products can be manufactured by injection molding the propylene polymer composition into various shapes under known conditions using a common injection molding apparatus. The injection molded products of the propylene polymer composition of the invention are antistatic and excellent in transparency, flexibility, heat resistance, impact resistance, surface gloss, chemical resistance and abrasion resistance to find wide applications in automobile interior trim materials, automobile exterior materials and containers.

Blow molded products can be made by blow molding the propylene polymer composition under known conditions using a common blow molding apparatus. For example, extrusion blow molding produces a hollow product by a series of steps in which the propylene polymer composition in a molten state at a resin temperature of 100 to 300° C. is extruded through a die to form a tubular parison, the parison is fixed in a mold of a desired shape, and air is blown to fit the parison into the mold at a resin temperature of 130 to 300° C. The draw (blowing) ratio is desirably about 1.5 to 5 times in the lateral direction.

Injection blow molding produces a hollow product by a series of steps in which the propylene polymer composition is injected at a resin temperature of 100 to 300° C. into a parison mold to form a parison, the parison is fixed in a mold of a desired shape, and air is blown to fit the parison into the mold at a resin temperature of 120 to 300° C. The draw (blowing) ratio is desirably 1.1 to 1.8 times in the longitudinal direction and 1.3 to 2.5 times in the lateral direction. The blow molded products of the propylene polymer composition possess high transparency, flexibility, heat resistance and impact resistance and have superior moisture proofness.

Press molded products include those by mold stamping. For example, such products are produced by press molding a substrate and a skin material simultaneously to integrate them (mold stamping forming) in which the propylene polymer composition constitutes the substrate.

The mold stamping formed products include automobile interior materials such as door trims, rear package trims, seat back garnishes and instrument panels.

Medical tubes of the propylene polymer composition can be manufactured using a common extruder and under known extrusion conditions. For example, the propylene polymer composition can be molten in a single screw extruder, a kneading extruder, a ram extruder or a gear extruder and be extruded through a circular die, followed by cooling.

The medical tubes may have a laminated structure according to need such as prevention of adsorption of chemicals to the inner surface or impartment of heat resistance, without impairment of the medical tube performance.

According to the present invention, there can be obtained the propylene polymer composition capable of giving formed products well balanced and excellent in transparency, impact resistance, flexibility, heat resistance, scratch resistance and rubber elasticity.

The medical tubes of the propylene polymer composition according to the present invention have well balanced properties such as transparency, kink resistance, flexibility, heat resistance, scratch resistance and rubber elasticity, and adequately satisfy the performance expected as medical tubes.

EXAMPLES

The present invention will be hereinafter described in greater detail by Examples, but it should be construed that the invention is in no way limited to those Examples.

The conditions for testing properties are as follows.

[Evaluation of Kink Resistance]

Figure 1:
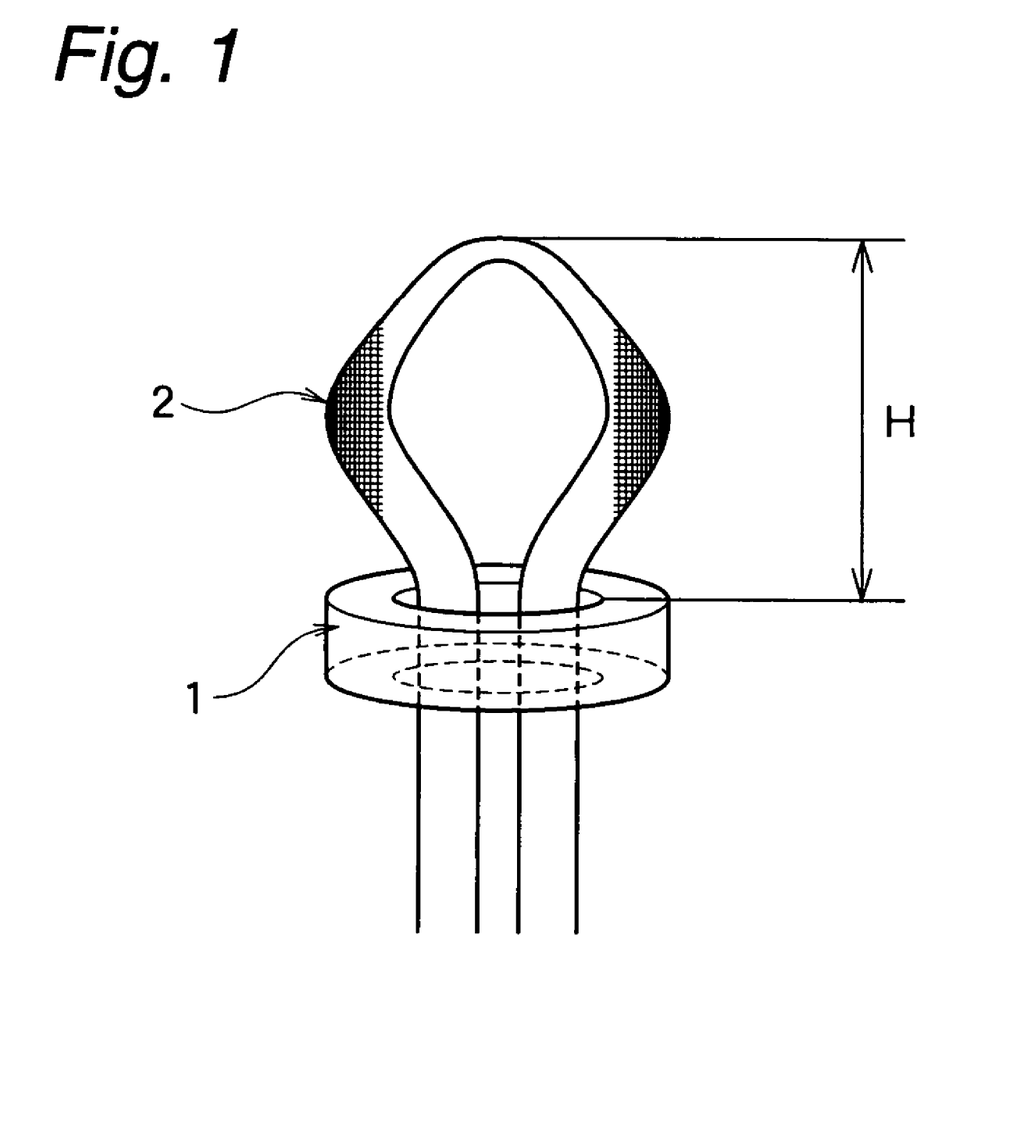

The evaluation employed a jig that was a hollow cylinder (1) having a hole 10 mm in diameter and 5 mm in height. A tube (2) having an inner diameter of 2.1 mm and a length of 20 cm was looped by inserting both ends thereof into the jig, and the both ends were slowly pulled down until a kink occurred in the loop. The loop length (H) at the occurrence of kink was obtained as indicator of the kink resistance.. The shorter the loop length, the higher the kink resistance. (See FIG. 1.)

[Measurement of Dynamic Viscoelasticity]

A specimen was twisted (torsion mode) at 10 rad/s over an area 10 mm width and 38 mm length and was heated from −100 to 100° C. at a heating rate of 2° C./min; the loss tangent tan δ and storage elastic modulus G' were measured at each temperature by means of Rheometrics RDS-II.

[Tensile Test]

1. Permanent Set

A dumbbell specimen 50 mm in length (L0), 15 mm in gauge length, 5 mm in width and 1 mmt in thickness that was fixed between chucks 30 mm apart was 100% strained (to a distance of 60 mm between the chucks) at a stress rate of 30 mm/min, maintained for 10 minutes and released for 10 minutes. The length (L) was measured and the permanent set was determined from the formula: Permanent set (%):=[(L−L0)/L0]×100.

2. Young's Modulus

A JIS No. 3 dumbbell specimen was tested for the Young's modulus with a span of 30 mm, at a stress rate of 30 mm/min and 23° C. in accordance with JIS K 6301.

[Heat Resistance]

Penetration Temperature (° C.)

A test specimen 1 mm thick was heated at a rate of 5° C./min and a plane indenter 1.8 mm in diameter was pressed at 2 kg/cm² in accordance with JIS K 7196. The penetration temperature (° C.) was determined from a TMA curve.

[Haze (%)]

A test specimen 1 mm thick was tested with digital turbidity meter NDH-20D manufactured by NIPPON DENSHOKU to determine the haze.

[Abrasion Resistance Test]

A test specimen 2 mm in thickness was tested with a "Gakushin" abrasion tester manufactured by Toyo Seiki Seisaku-Sho, Ltd., as follows. The tip of a 45R SUS abrasion indenter weighing 470 g was covered with a cotton duck No. 10, and was caused to abrade the specimen at 23° C., reciprocating 100 times at a reciprocating rate of 33 reciprocating motions per minute and with a stroke of 100 mm. The gloss change Δ Gloss between before and after the abrasion was determined by:

$$\Delta \text{ Gloss} = \frac{(\text{Gloss before abrasion} - \text{Gloss after abrasion})}{\text{Gloss before abrasion}} \times 100$$

[Melting Point (Tm) and Glass Transition Temperature (Tg)]

An endothermic curve was obtained by DSC, and the temperature at a maximum peak point was obtained as Tm. The measurement was performed as follows. A specimen was loaded into an aluminum pan and heated to 200° C. at a rate of 100° C./min. The temperature was maintained at 200° C. for 10 minutes and then lowered to −150° C. at a rate of 10° C./min. Then the temperature was raised at 10° C./min to obtain the endothermic curve.

[Intrinsic Viscosity [η]]

The intrinsic viscosity was measured at 135° C. in decalin.

[Mw/Mn]

Mw/Mn was measured by GPC (gel permeation chromatography) in an orthodichlorobenzene solvent at 140° C.

Synthetic Example 1

(Synthesis of Syndiotactic Polypropylene) (i-1)

Bulk polymerization of propylene was performed according to a method disclosed in JP-A-H02-274763, with use of a catalyst composed of diphenylmethylene (cyclopentadienyl) fluorenyl zirconium dichloride and methylaluminoxane and in the presence of hydrogen. The resultant syndiotactic polypropylene had a melt flow index of 4.4 g/10 min, a GPC molecular weight distribution of 2.3, a $^{13}$C-NMR syndiotactic pentad ratio (r.r.r.r) of 0.823, and Tm of 127° C. and Tc of 57° C. according to differential scanning calorimetry.

Synthetic Example 2

(Synthesis of Syndiotactic Propylene/Ethylene Copolymer) (ii-1)

A 1.5-liter autoclave vacuum dried and purged with nitrogen was charged with 750 ml of heptane at room temperature. A 1.0 mmol/ml toluene solution of triisobutylaluminum (hereinafter abbreviated to TIBA) was added in an amount of 0.3 ml to achieve the amount of 0.3 mmol in terms of aluminum atom. Thereafter, 50.7 liters (at 25° C. and 1 atmospheric pressure) of propylene was fed with stirring, and the temperature was raised to 30° C. The system was then pressurized with ethylene to 5.5 kg/cm²G. Subsequently, a heptane solution (0.0002 mM/ml) of diphenylmethylene(cyclopentadienyl) fluorenyl zirconium dichloride and a toluene solution (0.002 mM /ml) of triphenylcarbenium-tetra(pentafluorophenyl)borate synthesized by common processes were added in amounts of 3.75 ml and 2.0 ml respectively to initiate copolymerization of propylene and ethylene. The catalyst concentrations relative to the system were 0.001 mmol/liter for diphenylmethylene (cyclopentadienyl)fluorenyl zirconium dichloride and 0.004 mmol/liter for triphenylcarbenium-tetra(pentafluorophenyl) borate.

During the polymerization, the internal pressure was maintained at 5.5 kg/cm²G by continuously supplying ethylene. After 30 minutes from the initiation of the polymerization, the polymerization reaction was terminated by addition of methyl alcohol, followed by degassing. The polymer solution was recovered and was washed using an equivalent amount (1:1) of an aqueous solution containing 5 ml of concentrated hydrochloric acid per liter of water, and thereby the catalyst residues were transferred to the aqueous phase. The catalyst-mixed solution was allowed to stand, and the aqueous phase was separated and removed. The residue was washed twice with distilled water to complete separation of the polymerization liquid phase from the aqueous phase. The polymerization liquid phase thus separated was brought into contact with a three-fold amount of acetone with vigorous stirring to precipitate the polymer. After washing had been adequately performed with acetone, the solid phase (copolymer) was collected by filtration and was dried at 130° C. and 350 mmHg for 12 hours in a stream of nitrogen. The resultant propylene/ethylene copolymer weighed 50 g and had an intrinsic viscosity [η] at 135° C. in decalin of 2.4 dl/g, a glass transition temperature Tg of −28° C., an ethylene content of 24.0 mol % and a GPC molecular weight distribution (Mw/Mn) of 2.9. Any fusion peak was not substantially observed under the aforementioned DSC conditions.

Synthetic Example 3

(Synthesis of Syndiotactic Propylene/Ethylene Copolymer) (ii-2)

A 2000-ml polymerizer sufficiently purged with nitrogen was charged with 833 ml of dry hexane and triisobutylaluminum (1.0 mmol) at room temperature. The internal temperature of the polymerizer was raised to 90° C., and the pressure in the system was increased to 0.66 MPa by feeding propylene and was adjusted to 0.69 MPa with ethylene. Subsequently, a toluene solution of 0.001 mmol of diphenylmethylene (cyclopentadienyl) (octamethyldihydrobenzoylfluorenyl) zirconium dichloride and 0.3 mmol in terms of aluminum of methylaluminoxane (manufactured by Tosoh Finechem Corporation) was added into the polymerizer. Polymerization was carried out at an internal temperature of 90° C. for 20 minutes while maintaining the system pressure at 0.69 MPa with ethylene, and was terminated by addition of 20 ml of methanol, followed by degassing. The polymerization solution was poured into 2 liters of methanol to precipitate the polymer, and the polymer was vacuum dried at 130° C. for 12 hours. The resultant polymer weighed 46.4 g and had an intrinsic viscosity [η] of 2.31 dl/g, a glass transition temperature Tg of −24° C., an ethylene content of 19.0 mol % and a GPC molecular weight distribution (Mw/Mn) of 2.3. Any fusion peak was not substantially observed under the aforementioned DSC conditions.

Example 1

10 parts by weight of the syndiotactic homopolypropylene (i-1) obtained in Synthetic Example 1, and 90 parts by weight of the syndiotactic propylene/ethylene copolymer (ii-1) of Synthetic Example 2 were kneaded together to give a propylene polymer composition. The results are shown in Tables 1 and 2.

Example 2

The procedure of Example 1 was repeated, except that the syndiotactic propylene/ethylene copolymer (ii-1) was replaced with the syndiotactic propylene/ethylene copolymer (ii-2) obtained in Synthetic Example 3. The results are shown in Tables 1 and 2.

Example 3

9 parts by weight of the syndiotactic homopolypropylene (i-1) obtained in Synthetic Example 1, 81 parts by weight of the syndiotactic propylene/ethylene copolymer (ii-1) of Synthetic Example 2, and 10 parts by weight of a hydrogenated terpene resin (P125 manufactured by YASUHARA CHEMICAL CO., LTD., Tg=68° C., average molecular weight: 1100) (iii-1) were kneaded together to give a propylene polymer composition. The results are shown in Tables 1 and 2.

Example 4

The procedure of Example 3 was repeated, except that the syndiotactic homopolypropylene (i-1) was replaced with a propylene random copolymer (Polypro F337D manufactured by Sumitomo Mitsui Polyolefin Co., Ltd.). The results are shown in Tables 1 and 2.

Comparative Example 1

9 parts by weight of the syndiotactic homopolypropylene (i-1) obtained in Synthetic Example 1, 81 parts by weight of an ethylene/butene copolymer (TAFMER A4085 manufactured by Mitsui Chemicals, Inc.), and 10 parts by weight of a hydrogenated terpene resin (P125 manufactured by YASUHARA CHEMICAL CO., LTD., Tg=68° C., average molecular weight: 1100) (iii-1) were kneaded together to give a propylene polymer composition. The results are shown in Tables 1 and 2.

TABLE 1

| Items | Ex. 1 | Ex. 2 | Ex. 3 | Ex. 4 | Comp. Ex. 1 |
|---|---|---|---|---|---|
| Syndiotactic propylene (i-1) | 10 | 10 | 9 | | 9 |
| MFR (g/10 min) = 4.4 | | | | | |
| r.r.r.r = 0.823 | | | | | |
| Tm = 127° C. | | | | | |
| Tc = 57° C. | | | | | |
| Mw/Mn = 2.3 | | | | | |
| Isotactic propylene/ethylene random copolymer (F337D) | | | | 9 | |
| MFR (g/10 min) = 7 | | | | | |
| Tm = 131° C. | | | | | |
| Syndiotactic propylene/ethylene copolymer (ii-1) | 90 | | 81 | 81 | |
| C2 = 24 mol % | | | | | |
| [η] = 2.4 dl/g | | | | | |
| Tm: not observed | | | | | |
| Tg = −28° C. | | | | | |
| Mw/Mn = 2.9 | | | | | |

TABLE 1-continued

| Items | Ex. 1 | Ex. 2 | Ex. 3 | Ex. 4 | Comp. Ex. 1 |
|---|---|---|---|---|---|
| Syndiotactic propylene/ethylene copolymer (ii-2) C2 = 19 mol % [η] = 2.3 dl/g Tm: not observed Tg = −24° C. Mw/Mn = 2.3 | | 90 | | | |
| Ethylene/butene random copolymer (A4085) MFR (g/10 min) = 7 Density = 0.885 g/cm³ | | | | 81 | |
| Hydrogenated terpene resin (P125) Tg = 68° C. | | 10 | 10 | 10 | |

TABLE 2

| Items | Ex. 1 | Ex. 2 | Ex. 3 | Ex. 4 | Comp. Ex. 1 |
|---|---|---|---|---|---|
| Dynamic viscoelasticity | | | | | |
| (A) Loss tangent tanδ peak (peak value, temperature ° C.) | 1.0, −12° C. | 1.0, −9° C. | 1.2, −7° C. | 1.5, −10° C. | 0.3, −25° C. |
| (B) Storage elastic modulus G' × 10⁷ (dyn/cm², 20° C.) | 9.2 | 9.7 | 7 | 3.1 | 4.3 |
| (C) Penetration temperature (° C.) | 91 | 98 | 83 | 71 | 40 |
| (D) Permanent set (%) | 6 | 6 | 7 | 15 | 40 |
| Young's modulus (YM) (MPa) | 18 | 18 | 15 | 9 | 22 |
| Transparency (haze) (%) | 5 | 5 | 5 | 17 | 15 |
| Wear resistance (Δ Gloss) (%) | 20 | 18 | 25 | 37 | 90 |

Example 1b 10 parts by weight of the syndiotactic homopolypropylene (i-1) obtained in Synthetic Example 1, and 90 parts by weight of the syndiotactic propylene/ethylene copolymer (ii-1) of Synthetic Example 2 were kneaded together to give a propylene polymer composition. The composition was extruded using a tube forming machine (manufactured by PLA GIKEN CO., LTD.) constituted of a single screw extruder 40 mm in diameter fitted with a tube die, under the following conditions:

Extruder temperature setting:

C1/C2/C3/C4/H/D1/D2=190/200/200/200/200/200/200 (° C.)

Forming speed: 10 m/min

Tube size: 2.1 mm in inner diameter and 3.0 mm in outer diameter

The results of the measurements are shown in Table 1b.

Example 2b

The procedure of Example 1b was repeated, except that the syndiotactic propylene/ethylene copolymer (ii-1) was replaced with the syndiotactic propylene/ethylene copolymer (ii-2) obtained in Synthetic Example 3. The results of the measurements are shown in Table 1b.

Example 3b 9 parts by weight of the syndiotactic homopolypropylene (i-1) obtained in Synthetic Example 1, 81 parts by weight of the syndiotactic propylene/ethylene copolymer (ii-1) of Synthetic Example 2, and 10 parts by weight of a hydrogenated terpene resin (P125 manufactured by YASUHARA CHEMICAL CO., LTD., Tg=68° C., average molecular weight: 1100) (iii-1) were kneaded together to give a propylene polymer composition. A tube was formed under the same conditions as in Example 1. The results are shown in Table 1b.

Example 4b

The procedure of Example 3b was repeated, except that the syndiotactic homopolypropylene (i-1) was replaced with a propylene random copolymer (Polypro F337D manufactured by Sumitomo Mitsui Polyolefin Co., Ltd.). The results are shown in Table 1b.

Comparative Example 1b 9 parts by weight of the syndiotactic homopolypropylene (i-1) obtained in Synthetic Example 1, 81 parts by weight of an ethylene/butene copolymer (TAFMER A4085 manufactured by Mitsui Chemicals, Inc.), and 10 parts by weight of a hydrogenated terpene resin (P125 manufactured by YASUHARA CHEMICAL CO., LTD., Tg=68° C., average molecular weight: 1100) (iii-1) were kneaded together to give a propylene polymer composition. A tube was formed under the same conditions as in Example 1b. The results are shown in Table 1b.

TABLE 1b

| | Ex. 1 | Ex. 2 | Ex. 3 | Ex. 4 | Comp. Ex. 1 |
|---|---|---|---|---|---|
| Items | | | | | |
| Syndiotactic propylene (i-1) | 10 | 10 | 9 | | 9 |
| Isotactic propylene/ethylene random copolymer (F337D) | | | | 9 | |
| Syndiotactic propylene/ethylene copolymer (ii-1) | 90 | | 81 | 81 | |
| Syndiotactic propylene/ethylene copolymer (ii-2) | | 90 | | | |
| Ethylene/butene random copolymer (A4085) | | | | | 81 |
| Hydrogenated terpene resin (P125) | | | 10 | 10 | 10 |
| Measurement items | | | | | |
| Dynamic viscoelasticity | | | | | |
| (A) Loss tangent tanδ peak (peak value, temperature ° C.) | 1.0, −12° C. | 1.0, −9° C. | 1.2, −7° C. | 1.5, −10° C. | 0.3, −25° C. |
| (B) Storage elastic modulus G' × 10⁷ (dyn/cm², 20° C.) | 9.2 | 9.7 | 7 | 3.1 | 4.3 |
| (C) Penetration temperature (° C.) | 91 | 98 | 83 | 71 | 40 |
| (D) Permanent set (%) | 6 | 6 | 7 | 15 | 40 |
| Young's modulus (YM) (MPa) | 18 | 18 | 15 | 9 | 22 |
| Transparency (haze) (%) | 5 | 5 | 5 | 17 | 15 |
| Kink resistance (mm) | 22 | 20 | 23 | 32 | 50 |

INDUSTRIAL APPLICABILITY

The propylene polymer composition according to the present invention can give formed products well balanced and excellent in transparency, impact resistance, flexibility, heat resistance, scratch resistance and rubber elasticity.

The medical tubes of the propylene polymer composition according to the present invention have well balanced properties such as transparency, kink resistance, flexibility, heat resistance, scratch resistance and rubber elasticity, and adequately satisfy the performance expected as medical tubes.

The invention claimed is:

1. A propylene polymer composition satisfying all the following properties (A), (B), (C) and (D):
   (A) the composition shows a loss tangent (tan) peak at a temperature in the range of −20 to 25° C. according to dynamic viscoelasticity measurement (10 rad/s) in a torsion mode, and the peak value is 0.5 or above;
   (B) the storage elastic modulus G' at 20° C. from the dynamic viscoelasticity measurement is in the range of $1.0 \times 10^7$ to $4.9 \times 10^8$ dyn/cm$^2$;
   (C) the penetration temperature (° C.) determined in accordance with JIS K 7196 is in the range of 60 to 160° C.; and
   (D) the composition has a permanent set of not more than 20% as determined after the composition fixed between chucks 30 mm apart is 100% strained at a stress rate of 30 mm/min, maintained for 10 minutes and released for 10 minutes.

2. A propylene polymer composition comprising:
   (i) 1 to 40 parts by weight of a syndiotactic polypropylene; and
   (ii) 60 to 99 parts by weight of a syndiotactic propylene/ethylene copolymer that contains 99 to 55 mol % of a syndiotactic propylene component and 1 to 45 mol % of an ethylene component;
   wherein the composition has a Young's modulus (YM) of not more than 100 MPa as determined in accordance with JIS 6301.

3. The propylene polymer composition according to claim 2, wherein the syndiotactic polypropylene (i) has a syndiotactic pentad ratio (rrrr) determined by $^{13}$C-NMR of 0.5 or above, and a melt flow index (MFI) in the range of 0.1 to 50 g/10 mm; and the copolymer (ii) has an intrinsic viscosity [η] of 0.01 to 10 dl/g as determined at 135° C. in decalin, a molecular weight distribution determined by GPC of not more than 4, and a glass transition temperature Tg of not more than −10° C.

4. A medical tube comprising the propylene polymer composition of claim 1.

* * * * *